United States Patent [19]

Douglass

[11] 3,971,725

[45] July 27, 1976

[54] 2-MERCAPTOQUINOXALINE-1-OXIDES, SALTS THEREOF AND 2-(1-OXOQUINOXALINYL)DISULFIDES IN DETERGENT COMPOSITIONS

[75] Inventor: Miriam Lois Douglass, Bound Brook, N.J.

[73] Assignee: Colgate-Palmolive Company, New York, N.Y.

[22] Filed: Jan. 9, 1974

[21] Appl. No.: 431,824

Related U.S. Application Data

[62] Division of Ser. No. 303,778, Nov. 6, 1972, Pat. No. 3,852,443, which is a division of Ser. No. 808,413, Nov. 26, 1969, Pat. No. 3,733,323.

[52] U.S. Cl. ............................... 252/106; 252/107
[51] Int. Cl.$^2$ .................... C11D 3/48; C11D 9/50
[58] Field of Search .......................... 252/106, 107; 260/250 R; 424/250

[56] References Cited
UNITED STATES PATENTS

| | | | |
|---|---|---|---|
| 3,088,916 | 5/1963 | Roman | 252/106 |
| 3,091,613 | 5/1963 | Sasse et al. | 260/250 R |
| 3,177,218 | 4/1965 | Brown | 260/256.4 |
| 3,223,706 | 12/1965 | Sasse et al. | 260/250 R |
| 3,723,435 | 3/1973 | Furia et al. | 260/270 R |

Primary Examiner—P.E. Willis, Jr.
Attorney, Agent, or Firm—Herbert S. Sylvester; Murray M. Grill; Norman Blumenkopf

[57] ABSTRACT

2-mercaptoquinoxaline-1-oxides, salts thereof and 2-(1-oxoquinoxalinyl) disulfides are useful antimicrobial agents, active against gram-negative and gram-positive bacteria and fungi, e.q., *Escherichia coli, Bacillus subtilis, Micrococcus pyogenes* var. *aureus, Tricophyton mentagrophytes,* and *Pityrosporum ovale.*

The antimicrobial compounds are useful alone, usually in aqueous solution, as microbicides or microbistats. They may also be included as constituents of hairdressings or shampoo because they are effective microbicides, even in the presence of oily materials, such as the sebum normally secreted by the human scalp.

6 Claims, No Drawings

2-MERCAPTOQUINOXALINE-1-OXIDES, SALTS THEREOF AND -(1-OXOQUINOXALINYL)DISULFIDES IN DETERGENT COMPOSITIONS

This application is a divisional of application Ser. No. 303,778 filed Nov. 6, 1972 and issued Dec. 3, 1974 as U.S. Pat. No. 3,852,443, which was in turn a divisional of application Ser. No. 880,413 filed Nov. 26, 1969 and issued on May 15, 1973 as U.S. Pat. No. 3,733,323.

This invention relates to sulfur-containing quinoxaline derivatives which have been found to be useful against microorganisms. More specifically, the invention is of new compounds which are 2-mercaptoquinoxaline-1-oxides, salts thereof or 2-(1-oxoquinoxalinyl) disulfides. Also included within the invention are methods for the manufacture of such compounds, uses thereof and compositions containing them, especially hairdressings and shampoos, although other antimicrobial compositions are also included.

The extensive research undertaken by individuals and corporations in the chemical, drug and cosmetic fields, in their efforts to discover acceptable and effective antimicrobial agents, has resulted in the discovery of many useful compounds which have been incorporated in various preparations for industrial, agricultural, business, government or personal use, resulting in improved sanitary and hygienic conditions. These microbicides or microbistats include such diverse compounds as derivatives of mercury, arsenic, silver and iodine, quaternary ammonium compounds, peroxides, hypochlorites, sulfides, sulfanilamides, penicillins and many other inorganic and organic compounds, both relatively simple and highly complex. Some such compounds have been found to be especially useful in particular applications and others may have widespread areas of utility. However, it is the usual case that after extensive experimentation, particular antimicrobial compounds are found to be best for particular purposes. Thus, there are few bactericides or bacteriostats that are useful against all bacteria or, if useful against a wide variety of bacteria, economic and other considerations will generally dictate employment in particular applications.

A particularly difficult medium for successful employment of an antimicrobial compound is the human scalp and the hair thereon. Due to continued secretions of sebum and perspiration and deposits of dust, grease and oils on the scalp, often in part at least attributable to the use of preparations for treating the scalp and hair, particularly favorable conditions for the growth of microorganisms often prevail on the scalp. Even if the hair and scalp are washed fairly frequently, the growth of microorganisms there is generally faster than on most other parts of the human body and consequently, the actions of antimicrobial compounds employed thereon are often ineffective. However, by the use of the compounds of this invention, good activity is obtained against microorganisms, such as bacteria and fungi, even when they are growing in such a favorable environment as the human hair and scalp or in contact wih oily materials, such as human sebum.

The present compounds may be used in solutions, emulsions or suspensions, or as solids. They are usually in the forms of aqueous solutions or suspensions and may be applied to sites on which microbial growth is to be counteracted. For ease of application to such sites, they may be included in various carrier compositions and are considered to be especially useful in hairdressing preparations and in shampoos. They aid in killing microorganisms on various substrates, such as proteinaceous materials, e.g., skin, gelatin, hair, wool and leather. Also, they are compatible with various other hairdressing and shampoo constituents, and with many other cosmetics.

In accordance with the present invention there are provided 2-mercaptoquinoxaline-1-oxides of the formula:

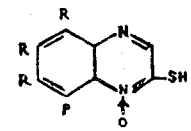

wherein R is hydrogen or an alkyl group of 1 to 12 carbon atoms, which may be the same as or different from other R's. Also, within the invention are the related 2-(1-oxoquinoxalinyl) disulfides of the formula:

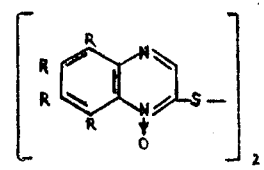

or salts of the 2-mercaptoquinoxaline-1-oxides of the formula:

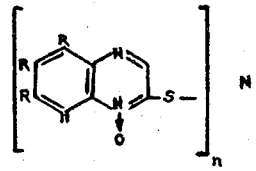

wherein R, which may be the same or different from other R's, is hydrogen or an alkyl group of 1 to 12 carbon atoms, and M is mono-, di- or trivalent metal, which is usually either alkali metal, an alkaline earth metal, a transition metal or a metal of one of groups III A, IV A or V A, ammonium or quaternary ammonium wherein the substituents on the quaternary nitrogen are alkyls of 1 to 18 carbon atoms or arylalkyls of 7 to 24 carbon atoms. Accordingly, $n$, representing the valence of M, will be 1, 2 or 3. The preferred 2-mercaptoquinoxaline-1-oxides are those wherein the R's are lower alkyl, usually of 1 to 4 carbon atoms, preferably of 1 to 2 carbon atoms, and wherein from 0 to 2 alkyl groups are present per molecule. Of these, those compounds are most preferred wherein R is hydrogen. As to the salts of the 2-mercaptoquinoxaline-1-oxides, those are preferred wherein M is an alkali metal, such as sodium, , an alkaline earth metal or a transition element, such as manganese. With respect to the mercaptoquinoxaline groups of derivative compounds, such as the 2-(1-oxoquinoxalinyl) disulfides, it is also preferred that from 0 to 2 R's should be on a quinoxaline group and that R should be of 1 to 4 carbon atoms, preferably of 1 to 2 carbon atoms. When two R's are present on the quinoxaline group, they should be in the 6 and 7 positions.

The invented compounds may be made from known starting materials by readily practiced processes. Starting wth quinoxaline, this is oxidized to quinoxaline-1,4- dioxide with 1.2 molar peracetic acid in acetic anhydride (melting point of the product equals 241.5°–242°C.). The yield obtained is 50 to 60% of theoretical. See Journal of the Chemical Society, page 2816 (1953, J. K. Landquist). The quinoxaline-1,4-dioxide is reacted with a 6 molar excess of benzenesulfonyl chloride and the greygreen solid obtained is then reacted with 10% aqueous sodium bicarbonate, to yield 2-chloroquinoxaline-1-oxide in 60% yield (m. p. equals 115°–116°C.). See Journal of General Chemistry, U.S.S.R., volume 34, page 2836 (1964, A. S. Elina). The reaction of 2-chloroquinoxaline-1-oxide with three molar equivalents of one molar aqueous sodium hydrosulfide results in a yellow aqueous solution of the sodium salt of 2-mercaptoquinoxaline-1-oxide. The yield is essentilly quantitative. The salt is convertible to the water-insoluble 2-mercaptoquinoxaline-1-oxide by precipitation thereof with an acid, such as concentrated aqueous hydrochloric acid. 2-(1-Oxoquinoxalinyl) disulfide is obtainable from 2-mercaptoquinoxaline-1-oxide by oxidation of the 2-mercaptoquinoxaline-1-oxide. Such oxidation may be effected with air (with the 2-mercaptoquinoxaline-1-oxide being oxidized by the air in a solvent such as acetone, methanol, ethanol or other suitable solvent, preferably at an elevated temperature such as that at which the solvent boils) or with other oxidizing agents, such as aqueous potassium triiodide, aqueous 3% hydrogen peroxide, or a dilute aqueous solution of a percarboxylic acid. Various other metal, ammonium or quaternary ammonium salts of 2-mercaptoquinoxaline-1-oxide may be obtained by treatment of a solution of a soluble salt thereof with an acid such as dilute hydrochloric acid or other suitable inorganic or organic acid, followed by addition of a dilute aqueous solution of the water soluble salt of the cation, e.g., a solution of the metal- or ammonium halide or sulfate.

The reactions described above are illustrated by the following equations:

For clarity of presentation, the above description of methods of making the invented compounds has been given with respect to a particular starting material and corresponding derivatives thereof. However, it must be realized that such methods are also applicable to reactions utilizing different starting materials and effected by different reagents, which are equivalent in their activities to those described. Thus, instead of utilizing quinoxaline as the starting material, 5,6,7,8,-tetramethylquinoxaline; 6,7-diethylquinoxaline; 6,7-dipropylquinoxaline; 5,8-dimethyl-6,7-dibutylquinoxaline, 6,7-di-n-hexylquinoxaline; 5-propylene tetramer quinoxaline; or 5,6-dimethyl-7-hexadecylquinoxaline or mixtures thereof may be employed as starting materials. The alkyl groups are preferably straight chain alkyls, terminally bonded to the quinoxaline ring, but branched chain alkyl and medially or non-terminally bonded alkyl groups may also be employed. From such materials, the corresponding quinoxaline-1,4-dioxides are made. Of course, the oxidation may be effected by any suitable mechanism, instead of employing peracetic acid in acetic anhydride. Also, various proportions of oxidizing agents may be employed, which will be known to those of skill in the art. Among other oxidizing reagents which can be used are perphthalic acid, permaleic acid, perbenzoic acid, and m-chloroperbenzoic acid. The solvents to be employed will be such as are conducive to dissolving the reagents and which are unaffected by the reaction.

The reaction of the quinoxaline-1,4-dioxide compound with benzenesulfonyl chloride or an equivalent material and the subsequent removal of the benzenesulfonic acid by treatment with aqueous sodium bicarbonate is a known reaction which the present inventor has shown to be useful in making the named substituted products, as well as 2-chloroquinoxaline-1-oxide. Of course, reagents other than benzenesulfonyl chloride which may have the same effect can be employed, as may be neutralizing materials other than sodium bicar-

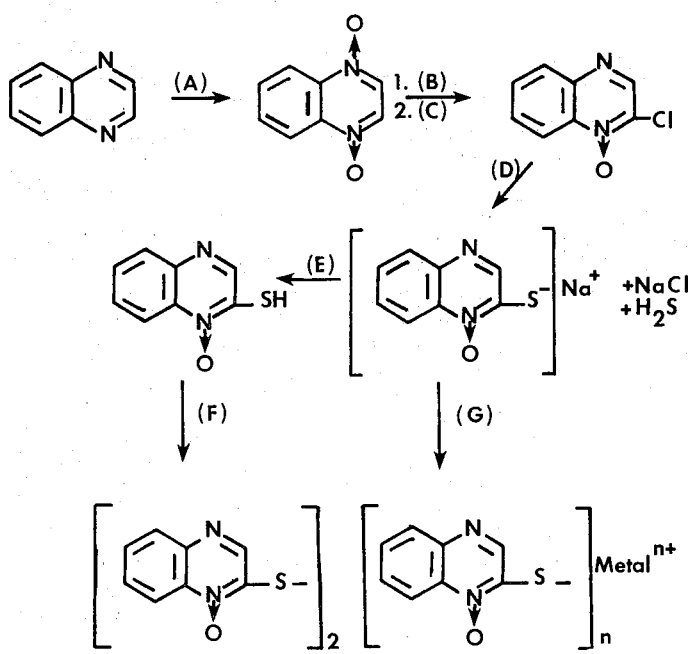

In the previous equations, A=1.2 molar $CH_3CO_3H$; D=$C_5H_5SO_2Cl$; C=$NaCCO_3$; D=1 molar NaSE (2moles); E=HCl; P=air, dilute $H_2O_2$, dilute $KI_3$ or dilute $RCO_3H$ (R=aryl or alkenyl); and C=$Metal^{n+}$.

bonate, with the end effect being to remove an oxygen atom from one of the nitrogens and to substitute a halogen atom for a hydrogen on a carbon adjacent to the remaining oxygen-containing nitrogen. The 2- haloquinoxaline-1-oxide or alkyl-substituted derivative thereof is next reacted with sodium hydrosulfide or other metal hydrosulfide, preferably an alkali metal hydrosulfide. The effect of this reaction, which is usually conducted in the aqueous phase, utilizing two to five molar equivalents of the metal hydrosulfide, preferably 3, is the production of a solution of the corresponding metal salt of 2-mercaptoquinoxaline-1-oxide. As will be seen from the previously given equation for this reaction it is a simple one in which the metal of the metal hydrosulfide is removed with the chlorine from the 2-chloroquinoxaline-1-oxide compound to form the metal chloride, the chlorine is replaced by the S-M group, and evolution of hydrogen sulfide completes the material balance. Instead of using the sodium or potassium hydrosulfide, although these are preferred, one may also employ hydrosulfides of other materials which form soluble salts. The proportion of hydrosulfide in the aqueous system employed is usually from 0.5 to 3 molar for best results. The soluble salt may be obtained from the solution by any of various known means, including evaporation, crystallization, selective absorption or adsorption or other known fractionating technique.

The salt of the 2-mercaptoquinoxaline-1-oxide may be converted to the corresponding 2-mercaptoquinoxaline-1-oxide compound by treatment with any suitable chemical for removing the salt-forming cation and replacing it with hydrogen. Thus, usually an aqueous soluton of solution acid, preferably a solution of a strong inorganic acid, such as hydrochloric acid or sulfuric acid, may be used to precipitate the 2-mercaptoquinoxaline-1-oxide compound. The stoichiometric quantity of acid will normally be employed, but variations are permissible. Of course, variations may also be made in the types of acid and the concentrations employed, provided that sufficient acid is used to convert the salt to the acid form. Other salts of the 2-mercaptoquinoxaline-1-oxides may be obtained by treatment of a soluble salt thereof with a soluble metal, ammonium or quaternary ammonium or other suitable inorganic or organic salt. If the alkali metal salt is more soluble, it will often be possible to convert to other salts, such as heavy metal salts, merely by addition of a soluble heavy metal salt to the alkali metal salt of 2-mercaptoquinoxaline-1-oxide, preferably in aqueous solutions. However, a preferred way to produce salts other than the alkali metal salts is to acidify an aqueous solution of an alkali metal salt to a pH of about 2.5-5.0, preferably a pH of about 4, with a dilute, strong, inorganic acid, such as hydrochloric acid or sulfuric acid, although other equivalent acids may also be employed, and to add to the acidified solution a dilute aqueous solution of the appropriate metal salt, preferably the halide or sulfate thereof. Again, it is preferred to employ approximately stoichiometric proportions of such salt and the corresponding alkali metal salt of 2-mercaptoquinoxaline-1-oxide, but variations, usually plus or minus 10 to 20% from stoichiometric proportions, are also useful. Among the salts that may be made from the alkali metal salts, e.g., the sodium, potassium and lithium salts of 2-mercaptoquinoxaline -1-oxide, are the zinc, calcium, magnesium, manganese, chromium, iron, copper, tungsten, nickel, barium, strontium ammonium and quaternary ammonium, e.g., catyltrimethyl ammonium, triethyloctadecyl ammonium and dibenzyldilauryl ammonium. The salts that may be employed include the corresponding chlorides, bromides, iodides, sulfates, phosphates, carbonates, borates, nitrates, acetates citrates, propionates. phenates, and the other useful water soluble salts.

From 2-mercaptoguinoxaline-1-oxide there may be produced the corresponding 2-(1-oxoquinoxalinyl) disulfide by oxidation. In such oxidation, as will be seen from the equations, hydrogen atoms adjacent to the sulfur of the 2mercaptoquinoxaline 1-oxide are removed, to be combined with oxygen to form water. Thus, the sulfur atoms bond together, forming the disulfide. Such oxidation may be effected by any suitable means, preferably utilizing air, another gaseous or chemical source of oxygen, or other oxidizing agents such as potassium triiodide, hydrogen peroxide, or percarboxylic acids.

The compounds produced, whether in the form of the 2-mercaptoquinoxaline-1-oxide compound or a salt thereof or in the form of the corresponding disulfide, exhibit exceptionally good antimicrobial properties. They are found to be effective in killing bacteria and in limiting the growths of various organisms. Thus they are very effective against the organism, *Micrococcus pyogenes* var. *aureus*, even when such organism is in a lipophilic environment, such as animal or mineral oil, fat or sebum. Often, when microorganisms are growing in such an environment, it is difficult to have an antimicrobial compound be effective against them, due to the inhibiting action of the grease or lipophilic material in the microbicide. Such inhibition may be either chemical or physical, whereby the lipophilic reacts with the antimicrobial compound to change it to a less effective compound or in which it prevents contact of the antimicrobial product with the microorganisms. In addition to the excellent utilities of the present compounds in such difficult environments, which are encountered on human or animal bodies and on the scalp or hair, it is found that these compounds are compatible with a wide variety of compositions and media in which they are employed. Thus, aqueous and alcoholic solutions of these compounds are useful, as are cosmetic preparations containing them, whether based on aqueous or lipophilic media or combinations of both such phases. For example, the present antimicrobial compounds may be used in cosmetics or detergents, including liquid, solid, and semi-solid paste, cream or gelatinous preparations. They may be employed in soaps, shampoos, hairdressings, dusting powders or talcs, foot powders, "aerosol" spray preparations of various types, anti-perspirants, deodorants, antiseptics and 8 other materials intended for cleaning, grooming or sanitizing purposes. Preferred compositions containing these compounds are those which are used in contact with the hair or scalp, such as shampoos and hairdressings. After use of such preparations, microbial counts on the hair and scalp are reduced, compared to a control. The 2-mercaptoquinoxaline-1-oxides, salts and the corresponding disulfides are effective against such potent gram-positive and gram-negative organisms as *Micrococcus pyogenes* var. *aureus* and *Escherichia coli* and the fungi *Pityrosporum ovale* and *trichophyton mentagrophytes*. Such effects of these compositions have not been noted before and the active antimicrobial compounds and compositions containing them have not been taught or suggested by the prior art.

The closest prior art reference known, wherein antibacterial activities are mentioned is U.S. Pat. No. 3,236,733, but that patent is for the use of pyridinethiones and oxides thereof which are substantially different from the present compounds. Also, although U.S. Pat. Nos. 2,537,870; 2,537,871; 3,157,654; and 3,249,610 describe compounds which bear some resemblances to the present compounds, they are not for the present compounds and do not make them obvious. The structurally closest reference compound found is in 94 Gasz. Chim. Ital. 3–30 (1964), wherein at page 17 and 30 formulas are given for 2-mercaptoquinoxaline-1-oxide. That reference discloses no method for the manufacture of the present compounds and the utilities of such compounds, described in this specification, are not mentioned in the reference.

In addition to the new compounds and methods for their manufacture, also within the present invention are cosmetic and detergent compositions containing such compounds as active antimicrobial ingredients, and antimicrobial uses of the compounds and such compositions. It is considered that the present microbicides are useful in a wide variety of cosmetics and antimicrobial preparations, including hairdressings, hair tonics, hair waving solutions, hair dyes, bleaches, rinses, face creams, face powders, foot powders, body lotions, tanning agents, antiperspirants, sunscreens, personal deodorants, makeup preparations, bath oils, facial treatments, astringents, shaving creams, after-shave lotions and various other preparations for treatment of the hair or skin, in which antibacterial or antifungal activity is useful. Among the detergent compositions which can usefully include the present antimicrobial compounds are bar soaps, liquid soaps, soap shampoos, synthetic detergent shampoos, heavy duty synthetic organic detergents, inorganic detergent salts, pre-soak compositions, which may include enzymes, softeners, dishwashing products, synthetic detergents intended for washing hard surfaces, e.g., janitorial detergents, floor cleaning compositions and other detergent-related products such as wax-removers, organic solvent solutions of surface active materials, compositions for employment with steam cleaning machinery, car washes, and sterilizing preparations.

The cosmetic compositions may contain from 0.1 to 99% of active ingredients for the primary purpose for which they are intended, together with from 0.1 to 20%, preferably from 0.1 to 3% of a compound of the present invention. Usually, the cosmetics will contain from 1 to 100% of an aqueous or an oily phase or a solid material and sometimes, as in the cases of emulsions, will contain both aqueous and oily phases, often with a surface active material to aid in emulsification. Such surface active agents may be anionic, nonionic, cationic or amphoteric and are usually present in emulsified cosmetics in proportions from 0.5 to 20% thereof.

Although the most preferred embodiments of the invention, hairdressings or other preparations intended for application to the hair, may be essentially lipophilic, essentially hydrophilic or emulsions, and may even be inert powders, the present compounds may be employed in any such medium. If the medium is lipophilic, there will usually be present from 50 to 99% of oil, such as mineral oil, lanolin, lanolin derivatives or other lipophilic materials, together with one or more of the present compounds. A solvent, e.g., a lower alkanol such as ethanol or isopropanol, may also be used to thin the lipophilic phase to make it easier to apply. It will usually be from 5 to 80% of the cosmetic. If the preparation is hydrophilic, it will usually contain from 50 to 99% of water, sometimes with 5 to 40% lower alkanol solvent associated therewith, plus one or more of the present antimicrobial compounds. The emulsions may have from 1 to 99%, usually from 20 to 80% of either lipophilic or hydrophilic materials, with essentially the balance thereof being of the other type. The various active ingredients utilized to give the different cosmetic preparations their desired properties are well known and are exhaustively described in the text by Edward Sagarin, Cosmetics Science and Technology (1957), and therefore, will not be listed here. However, for example, it is mentioned that with respect to hairdressings, ordinarily a mineral oil and lanolin will be employed to condition the hair and facilitate its taking of waving or combing.

Antiperspirants will normally contain an active chemical for such purpose, such as aluminum chlorohydrate. Dusting powders will normally be based on talc, silica, or other special form of such materials, such as pyrogenic silica. Skin creams or lotions will usually include stearic acid or other cold cream ingredients. The proportions of such active materials as was previously mentioned, may be varied widely, as is known in the art.

The detergent compositions in which the present antimicrobial compounds are useful may be either built or unbuilt products and may be based on anionic, cationic, nonionic and/or amphoteric surface active compounds. These are well known and are described in the text by Schwartz, Perry and Berch, Surface Active Agents and Detergents, Volume II, (1958), particularly at pages 321 and 621 – 625. Most frequently, the detergents employed will be anionic detergents, including the common higher fatty acid soaps of alkali metals and the synthetic anionic organic detergent salts such as those which are currently commercially used.

As examples of the anionic synthetic organic detergents there may be mentioned the higher alkane sulfonates, higher fatty acid monoglyceride sulfates, linear higher alkyl benzene sulfonates, higher fatty acid soaps, polyoxyethylene sulfates, hydroxyalkylene sulfonates, higher alcohol sulfates, salts of lower alcohol esters of sulfofatty acids, aromatic polyethoxy ether sulfates, acyl sarcosinates, acyl esters of isethionates and acyl N-methyl taurides, to name only a few. The salt-forming metals or other suitable salt-forming radicals for the detergents are preferably alkali metal, such as potassium or sodium but alkaline earth metals, ammonium, alkylamine, alkarolamine and magnesium salts may also be used. Some specific examples of these detergents are sodium lauryl sulfate; sodium linear tridecyl benzene sulfonate; triethanolamine lauryl sulfate; sodium or potassium coconut oil - tallow soaps; sodium lauryl sulfonate; potassium hexadecylnaphthalene sulfonate; lauryl alcohol ethylene oxide sulfate comprising four ethoxy groups per molecule; potassium stearyl glyceryl ether sulfonate; sodium lauryl sarcosinate; and magnesium methyl tauride.

Among the nonionic surface active agents are the condensation products of alkylated phenols of ethylene oxides, alkylthioethanols with ethylene oxide, higher fatty alcohols with ethylene oxide and polyalkylene glycols or other polyols with lower alkylene oxides. Among the cationic surface active materials are N-2-aminoethyl higher alkyl amines; N-2-aminoethyl higher fatty acid amides; and quaternary ammonium compounds wherein an alkyl group is of 12 to 18 carbon atoms and other groups attached to the nitrogen are alkyls of 0 to 3 carbon atoms. Among such are ethyl-dimethylstearyl ammoniun chloride; benzyl dimethylstearyl ammonium chloride; and trimethylcetyl ammonium bromide. The amphoteric detergents, containing both anionic and cationic groups, include the N-higher alkyl betaines, and related compounds of this class. Also suitable are the fatty imidazolines and betaines containing a sulfonic group instead of the carboxylic radical.

In the built detergents, water soluble inorganic salt builders or organic builders are present to assist in dispersing, peptizing, sequestering, and alkalizing, whereby detergency is increased. Among these are the pyrophosphates, tripolyphosphates, silicates, borates, carbonates, sesquisilicates and other water soluble alkaline salts, for which the salt-forming metal is usually an alkali metal, such as sodium or potassium.

Generally, in the detergent compositions, the proportion of detergent will be from 5 to 99% and preferably, there will be present from 10 to 50% thereof. The builder salts, when present will normally be from 15 to 60% of the composition and the active antimicrobial compound will be from 0.1 to 20% thereof, preferably from 0.1 to 5% thereof and most often will be from 0.5 to 3% of the total product. The balance of such compositions will usually be an adjuvant or mixture thereof, being ordinarily from 0.1 to 25%, in total. Such adjuvants include perfumes, dyes, bleaches, softening agents, anti-redeposition agents, emollients, and brighteners. In the preferred detergents, which are essentially unbuilt shampoo preparations, there will be present from 5 to 35% of soap or synthetic organic detergent or mixture thereof, from 0.1 to 5% of antimicrobial compound and from 1 to 20% of various adjuvants, such as thickeners, foaming agents, perfumes, coloring materials, and conditioning agents. The balance will be water, with possibly from 5 to 25% of lower alkanol, if desired.

The present antimicrobial preparations, cosmetics or detergents are used in accordance with normal techniques. Thus, to sterilize or make antimicrobial a particular surface, a suitable solution of the present 2-mercaptoquinoxaline-1-oxide or other compound of this invention may be applied to the surface and allowed to remain there or it may be removed by rinsing after a suitable time. The detergents and cosmetics are used in normal fashion. The 2-mercaptoquinoxaline-1-oxide, its salt or the disulfide act to kill bacteria and fungi while on the surface which is a locus thereof, making such locus sterile or significantly decreasing the counts of microorganisms. Of course, the amount or proportion of antimicrobial compound(s) in the preparations employed, whether solutions or more complex compositions, is enough to be effective for the particular use. When the microbicide is not completely removed from the surface, by rinsing or other means, the portion remaining acts to prevent bacterial and/or fungus growths thereon. Germicidal activity is important when the compositions are applied to the human hair and scalp, to obtain their antibacterial effects. In part, such activity might be attributed to the presence of sulfur in the invented compounds. Various of the present compounds are found to be especially useful against bacteria and fungi which normally are resident in the hair such as *Micrococcus pyogenes* var. *aureus* and *Pityrosporum ovale*.

The following examples are given to illustrate specific preferred embodiments of this invention. Clearly, the invention is not limited thereto. All temperatures are given in degrees Centigrade and all parts are by weight, unless otherwise indicated.

EXAMPLE 1

1 gram mole of quinoxaline (130 g.) is oxidized by treatment with 3150 milliliters of a 1.2 molar solution of peracetic acid in acetic anhydride, according to the method of Landquist, reported in the Journal of the Chemical Society at page 2816 (1953). The product, quinoxaline-1,4-dioxide, having a melting point of between 241.5° and 242.0°C. (with decomposition), is obtained in 50–60% yield. It is reacted with 530 grams of benzenesulfonyl chloride at a temperature of 25°C. for 1 to 12 hours and the resulting grey-green solid product is treated with 440 milliliters of a 10% aqueous solution of sodium bicarbonate, to produce 2-chloroquinoxaline-1-oxide. The product obtained has a melting point of 115°–116°C. after crystallization from cyclohexane or methanol. It is obtained in approximately 60% yield. The method for this reaction is reported in the Journal of General Chemistry, V.S.S.R., volume 34, page 2836 (1964).

The 2-chloroquinoxaline-1-oxide is added to 900 milliliters of a one molar aqueous solution of sodium hydrosulfide. The temperature of the reaction is 25°C. and byproduct $H_2S$ is vaporized off, leaving a yellow aqueous solution of the sodium salt of 2-mercaptoquinoxaline-1-oxide in essentially quantitative yield.

When the aqueous solution of the sodium salt of 2-mercaptoquinoxaline-1-oxide is treated with concentrated aqueous hydrochloric acid (11.6N) at a temperature of 25°C. until the pH of the suspension reaches 2, 2-mercaptoquinoxaline-1-oxide is precipitated. The product has a melting point of 124.5°—125.4°C. and the precipitate is obtained in 90% yield.

Analysis: Calculated for $C_8H_6N_2OS$: C=53.9%; H=3.4%; N=15.7%; S=18.0%. Found: C=54.5%; H=3.3%; N=15.6%; S=18.2%.

Instead of quinoxaline, corresponding alkyl-substituted derivatives thereof may be employed as starting materials, oxidizable to the corresponding 1,4-dioxides. Thus, quinoxaline substituted in the 5,6,7 and 8 positions by methyl, butyl or hexyl may be used as may be 5,6-dimethyl-7hexadecyl quinoxaline and 5-dodecyl quinoxaline, among other such compounds. The products obtained by treatment of the dioxides with benzenesulfonyl chloride may be neutralized with other neutralizing agents, e.g., sodium carbonate, sodium hydroxide, potassium carbonate, lithium hydroxide, manesium hydroxide or zinc carbonate.

To make the desired salts of 2-mercaptoquinoxaline-1-oxide, other hydrosulfides such as potassium hydrosulfide, lithium hydrosulfide or magnesium hydrosulfide may be used. Also, to precipitate the acid form of 2-mercaptoquinoxaline-1-oxide or alkyl-substituted derivatives thereof, there may be employed gaseous hydrogen chloride, sulfuric acid, acetic acid or any other suitable acid, although strong inorganic acids in aqueous solution are preferred.

EXAMPLE 2

1 gram mole of the sodium salt of 2-mercaptoquinoxaline-1-oxide (200 grams) in 2.9 liters of aqueous or aqueous alcoholic solution is reacted with the stoichiometric proportion of zinc chloride or manganous sulfate. The reaction is carried out at about room temperature and the insoluble zinc or manganous salt of 2-mercaptoquinoxaline-1-oxide is recovered by filtration.

Analysis: calculated for $C_{16}H_{10}N_4O_2S_2Zn$: C=45.6%; H=2.4%; H=13.4%. Found: C=45.8%; H=2.5%; N=13.3%.

Analysis: Calculated for $C_{16}H_{10}N_4O_2S_2Mn$: C=47.0% H=2.5%; N=13.7%.

Found: C=47.0%; H=2.9%; N=14.1%.

Alternatively, such compounds are also produced from 2-mercaptoquinoxaline-1-oxide, sodium salt, after acidification of an aqueous solution thereof with dilute hydrochloric acid and subsequent addition of a dilute aqueous solution of zinc chloride or manganous sulfate. In such reactions, the specific proportions of ingredients are not important. Although it is preferred to employ dilute aqueous solutions of the reactants and generally enough of the heavy metal or other metal salt will be used to replace completely the more soluble sodium salt.

Instead of the sodium salt of 2-mercaptoquinoxaline-1-oxide as starting material, corresponding alkali metal salts may be employed, e.g., the potassium salt. Also, the metals replacing the alkali metal cation may be aluminum, chromium, copper, nickel, calcium, magnesium or other suitable alkaline earth metal, transition metal or Group III A, IV A or V A metal. Also, the other salts of 2-mercaptoquinoxaline-1-oxides, described in Example 1 above, may be employed as starting materials, with the production of the corresponding salts. Instead of the metal salts, when quaternary ammonium salts, such cetyltrimethylammonium bromide or dimethyl benzyl lauryl ammonium chloride are reacted with the sodium salt of 2-mercaptoquinoxaline-1oxide, the quaternary ammonium derivatives are made. Such compounds combine antibacterial activities of both the quaternary-type product and the 2-mercaptoquinoxaline-1-oxide structure.

EXAMPLE 1

1 gram mole of 2-mercaptoquinoxaline-1oxide -ovide 178 grams) is dissolved in boiling acetone and is oxidized by the passage of air through the boiling solution. In place of acetone, methanol or ethanol or other suitable low boiling solvent may also be employed. Alternatively, oxidation may be accomplished by the addition of stoichiometric quantities of a 0.1 molar aqueous solution of potassium triiodide, a 3% aqueous solution of hydrogen peroxide, or a dilute solution of a percarboxylic acid to a suspension of 2-mercaptoquinoxaline-1-oxide in the water. The oxidations produce the disulfide, 2-(1-oxoquinoxalinyl) disulfide.

Analysis: Calculated for $C_{16}H_{10}N_4O_2S_2$; C=54.2%; H=2.8%; N=15.8%; S=18.1 %. Found: C=53.8%; H=2.8%; N=15.9%; S=18.8%.

Corresponding alkyl-substituted disulfides are produced when the starting material is substituted at the 5,6,7 or 8 position or all or any of such positions with a lower alkyl, e.g., methyl, ethyl. The disulfides are recovered in nearly quantitative yields by filtration and evaporation of the solvent.

EXAMPLE 4

Compounds produced as described in the preceding examples are formulated into cosmetic and detergent compositions by addition thereof to conventional detergent or cosmetic formulations. The most prefered antimicrobial compounds of this invention, in such applications, are the metal salts. The most preferred cosmetic is a hairdressing, while the best detergent formulation is a shampoo. Therefore, 1.0% of the sodium, manganese or zinc salt of 2-mercaptoquinoxaline-1-oxide is incorporated in shampoos comprising 15% potassium hexadecyl sulfate; 15% sodium coco-fatty acids monoglyceride sulfate; 5% coconut oil fatty acids diethanolamide; 3% lauric myristic monoethanolamide;1% perfume, 1% lanolin esters; 0.2% sodium carboxymethyl cellulose; 1.5% free oil; 2% glycerine and the balance water. When used to wash human hair, the bacterial count thereon is substantially decreased, when compared with a control not containing these bactericides. Also, fungal growth is inhibited When the detergent solution is applied to hard surfaces, either with an additional builder added, such as 20% of sodium tripolyphosphate, in replacement of some of the water, or without builder, a similar effect is obtained. Such results are also obtainable by utilizing other shampoo formulations, based on nonionic or cationic detergents or other of the previously mentioned synthetic detergents instead of the mentioned combination of anionic detergents. A similar result is noted when the shampoo is based on soluble higher fatty acid soap. Usually, for shampoo applications, the milder of the mentioned detergents will be seleced, so as to avoid unduly drying or embrittling the hair.

Hairdressings of various types are made, to which are added various proportions of antimicrobial compounds of this invention. Among these formulas are the following:

| (A) | Percent |
|---|---|
| Light mineral oil | 72.0 |
| Isopropyl myristate | 22.0 |
| Lanolin | 2.0 |
| Lanolin esters | 1.5 |
| Perfume | 1.2 |
| Sodium salt of 2-mercaptoquinoxaline-1-oxide | 1.3 |

| (B) | |
|---|---|
| Light mineral oil, white deodorized | 45.0 |
| Stearic acid | 5.0 |
| Cetyl alcohol | 2.0 |
| Triethanolamine | 2.5 |
| Perfume | 0.7 |
| Zinc salt of 2-mercaptoquinoxaline-1-oxide | 2.0 |
| water | 42.0 |

| (C) | |
|---|---|
| Sodium carboxymethyl cellulose | 1.0 |
| Polyethylene glycol 600 laurate | 10.0 |
| Propylene glycol laurate | 2.0 |
| Ethanol | 30.0 |
| Perfume | 1.0 |
| Lanoline esters | 2.0 |
| Manganese salt of 2-mercaptoquinoxaline-1-oxide | 0.7 |
| Water | 53.3 |

When human hair and the scalp are treated with the above compositions, using approximately three cubic centimeters per application, the presence of the 2-mercaptoquinoxaline-1-oxide salt counteracts microbial growth. By repeated daily usage over a period of weeks, diminished microbial counts are continually obtained. The compositions are especially useful with respect to diminishing the bacterial counts of *Micrococcus pyogenes* var. *aureus*. Also, they are useful with respect to diminishing other bacterial and fungal counts and in particular, the sodium salt of 2-mercaptoquinoxaline-1-oxide is especially effective against *Pityrosporum ovale*, even in the presence of sebum.

In place of the particular salts of 2-mercaptoquinoxline-1-oxide of the above formulas, similar proportions or variations in proportions, within the ranges described in the specification, may be employed with respect to other salts, e.g., the copper, nickel, chromium, trimethylcetyl ammonium, ammonium, alkanolamine and other such salts, the acid form and the disulfide, with the obtaining of similar antimicrobial activities. It is noted that the bactericides are especially useful against *Micrococcus pyogeneo var. aureus* even in sebum, which is present in the normally oily environment of the scalp and hair. They are also effective in the lipophilic phases of hairdressings.

Similar results are obtained when the mentioned bactericides are used in similar proportions in other cosmetics, e.g., hair setting compositions, "aerosol" hair sprays, hair dyes, skin creams, talcum powders and foot powders.

The surface active agents used in the above preparations and in the present cosmetics, for their emulsifying, weting or cleaning properties, may also include those mentioned in the previous specification as constituents of detergents and shampoos.

EXAMPLE 5

In addition to in vivo activity of the present compounds in various cosmetic and detergent formutations, laboratory experiments prove the effectiveness of the various active ingredients against representative microbes. Thus, when tested by a standard in vitro test employed to determine effectiveness of antimicrobial compounds, significant activities obtain for 2-mercaptoquinoxaline-1-oxide, its disulfides and various metal salts thereof, including the sodium, manganese, zinc, and other metal salts, such as the copper, magnesium, calcium, lithium, potassium and nickel salts.

One test employed is known as the paper disc agar plate diffusion method. In this test, a one-quarter inch disc of filter paper is saturated with an aqueous solution of microbicide and surface active agent, after which it is dried. The microbicide and the surface active agents are each present to the extent of 1% in the solution. The microbicide is a salt of 2-mercaptoquinoxaline-1-oxide and the detergent is either an ordinary sodium soap of mixed coconut oil and tallow fatty acids or is sodium lauryl sulfate. The agar plate is prepared by depositing a thin layer of agar-agar in a Petri dish. This is inoculated with the microorganism, in some cases with sebum or other possibly interforing lipophilic material also being present. The paper discs are placed on the agar-agar plate in replicates of four per sample and are incubated in a 35°C. oven. After 4 days, the microbial growth on the plate in area unaffected by the germicide is significant. However, about the various discs containing the present germicides, zones of inhibition are noted, indicating the effectiveness of the bactericides against the organism employed.

When tested against *Micrococcus pyogeneo*,var. *aureus*, that microorganism plus sebum, and *Pityrosporum ovale*, with or without sebum, it is found that the sodium salt of 2-mercaptoquinoxaine 1-oxide is outstanding. Also, the zinc and maganese salts of 2-mercaptoquinoxaline-1-oxide exhibit activity against *Micrococcus pyogenes*var. *aureus*, with the manganese salt being better than the zinc salt in this respect. Similar results against bacteria and fungi are also obtainable when other salts of 2-mercaptoquinoxaline-1-oxide, such as the copper, nickel, potassium, lithium, chromium and ammonium salts are employed. such results also obtain when the compound tested is 2-mercaptoqulnoxaline-1-oxide or disulfide.

When a serial dilution test of antimicrobial activity is used to evaluate various compounds of this invention it is found that the sodium, zinc, nickel and manganese salts of 2-mercaptoquinoxaline-1-oxide are most effective are *S.aureus; S. aureus* the sodium, zinc and manganese salts are most effective against *Str, mitis* and *B. subtilis;* the sodium and zinc salts are most effective against *E. coli;* the sodium and manganese salts are most effective against yeasts (*P. ovale*); and the sodium, nickel and manganese salts are best against molds (*T. mentaphytes*). By such tests, the disulfide is most effective against *Str. mitis*, *B. subtilis* and *P. ovale*, of the various microorganisms against which it is tested. Of course, while the above-mentioned results are reported for the most effective compounds of the invention, other such compounds also exhibit significant antimicrobial activites, as had been previously mentioned.

The invention has been described with respect to various illustrations and embodiments thereof. However, the invention is broader than the illustrations given and it will be evident to one of ordinary skill in the art that substitutes and equivalents may be employed, within the invention concept.

What is claimed is:

1. A detergent composition which includes an anionic, cationic, nonionic, or amphoteric surface active compound and a fungicidal or bactericidal amount of a compound selected from the group consisting of 2-mercaptoquinoxaline-1-oxides of the formula:

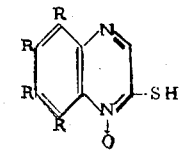

salts thereof of the formula

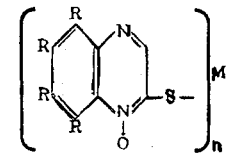

and disulfides thereof of the formula

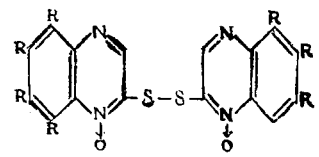

wherein R is hydrogen or an alkyl group of 1 to 12 carbon atoms, M is selected from the group consisting of alkali metals, alkaline earth metals, transition element metals, Group III-A metals, Group IV-A metals, Group V-A metals, ammonium and quaternary ammonium, wherein the substituents on the quaternary nitrogen are selected from the group consisting of alkyl groups of 1 to 18 carbon atoms, and arylalkyl groups of 7 to 24 carbon atoms, and n, representing the valence of M, is either 1, 2 or 3.

2. A composition as defined in claim 1 containing 0.5 to 99% of said surface active compound and 0.1 to 20% of said mercaptoquinoxaline compound.

3. A composition as defined in claim 2 containing an anionic surface active compound.

4. A composition as defined in claim 3 containing a builder selected from the group consisting of the alkali metal pyrophosphates, tripolyphosphates, silicates, borates, carbonates, and sesquisilicates.

5. A composition as defined in claim 1 which is a shampoo.

6. A composition as defined in claim 5 containing 5 to 35% of said surface active compound and 0.1 to 5% of said mercaptoquinoxaline compound.

* * * * *